(12) United States Patent
Anderson et al.

(10) Patent No.: US 6,669,652 B2
(45) Date of Patent: Dec. 30, 2003

(54) GUIDEWIRE WITH TAPERED DISTAL COIL

(75) Inventors: David M. Anderson, Temecula, CA (US); Emmanuel C. Biagtan, Temecula, CA (US); Wayne E. Cornish, Fallbrook, CA (US); Sharon Y. Wong, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/748,089

(22) Filed: Dec. 21, 2000

(65) Prior Publication Data

US 2002/0082524 A1 Jun. 27, 2002

(51) Int. Cl.[7] .......................... A61B 5/00; A61M 25/00
(52) U.S. Cl. ..................................... 600/585; 600/434
(58) Field of Search ................... 600/585, 434, 600/435

(56) References Cited

U.S. PATENT DOCUMENTS

| | | | |
|---|---|---|---|
| 3,973,556 A | * | 8/1976 | Fleischhacker et al. ..... 600/585 |
| 4,534,363 A | * | 8/1985 | Gold ........................... 600/585 |
| 4,619,274 A | | 10/1986 | Morrison |
| 4,748,986 A | | 6/1988 | Morrison et al. |
| 4,884,579 A | | 12/1989 | Engelson |
| 5,001,825 A | | 3/1991 | Halpern |
| 5,107,852 A | | 4/1992 | Davidson et al. |
| 5,108,368 A | * | 4/1992 | Hammerslag et al. ...... 604/528 |
| 5,111,829 A | | 5/1992 | Alvarez de Toledo ...... 128/772 |
| 5,238,004 A | | 8/1993 | Sahatjian et al. ........... 128/772 |
| 5,259,393 A | | 11/1993 | Corso, Jr. et al. |
| 5,303,714 A | | 4/1994 | Abele et al. ................. 128/772 |
| 5,333,620 A | | 8/1994 | Moutafis et al. ............ 128/772 |
| 5,433,200 A | * | 7/1995 | Fleischhacker ............. 600/585 |
| 5,622,184 A | | 4/1997 | Ashby et al. ............... 128/772 |
| 5,840,046 A | | 11/1998 | Deem |
| 6,042,876 A | | 3/2000 | Deem |
| 6,329,069 B1 | * | 12/2001 | Azizi et al. ................. 428/600 |
| 2002/0095102 A1 | * | 7/2002 | Winters ....................... 600/585 |

* cited by examiner

*Primary Examiner*—Charles A. Marmor, II
(74) *Attorney, Agent, or Firm*—Paul Y. Feng; Fulwider Patton Lee & Utecht, LLP

(57) ABSTRACT

A guidewire having a flexible coil with a tapered distal tip. Preferably, the flexible coil has a polymer coating at least at its tapered distal portion. The polymer coating may comprise polyurethanes or other suitable polymers. The guidewires of the invention provide desirable performance characteristics, particularly when used to cross relatively tight lesions such as chronic total occlusions.

8 Claims, 1 Drawing Sheet

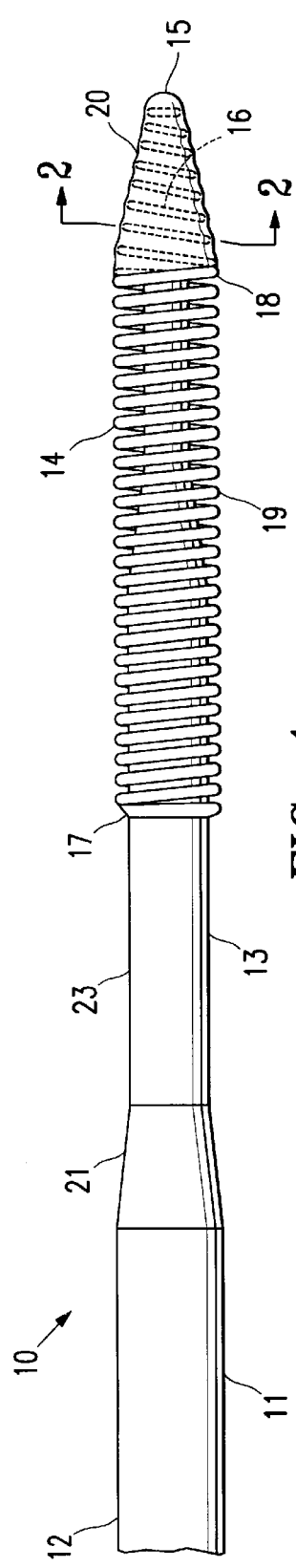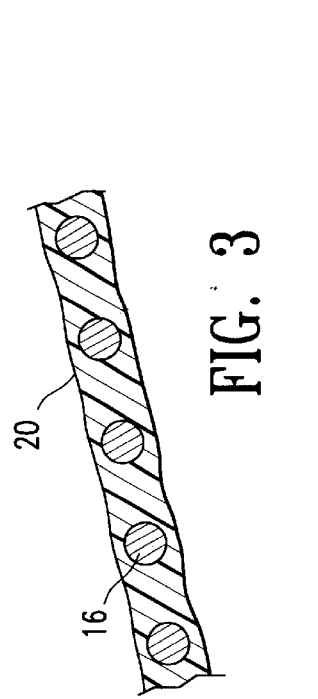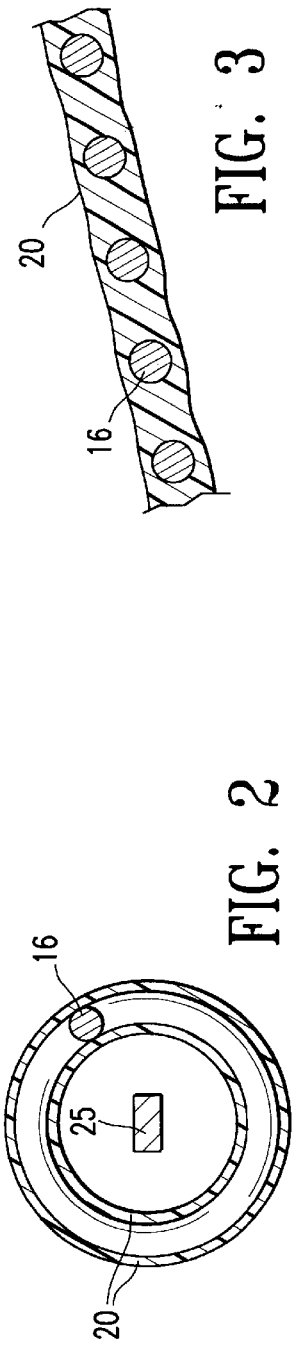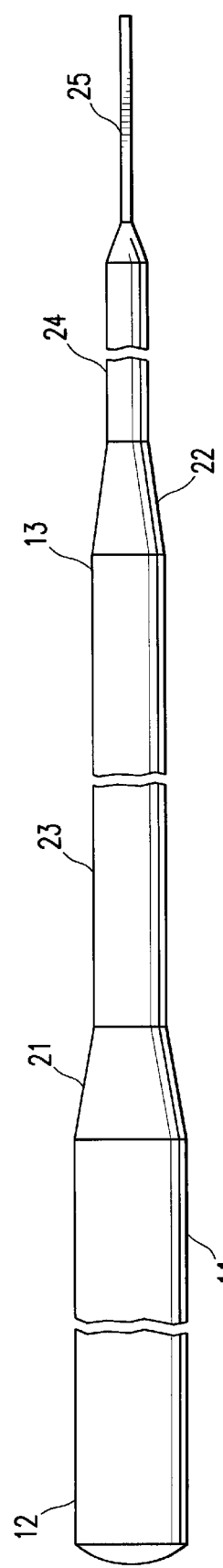

GUIDEWIRE WITH TAPERED DISTAL COIL

BACKGROUND OF THE INVENTION

The invention relates to the field of intravascular guiding members. In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. Conventional guidewires for angioplasty and other vascular procedures usually comprise an elongated core member with one or more tapered sections near the distal end thereof and a flexible body such as a helical coil disposed about the distal portion of the core member. Torquing means are provided on the proximal end of the core member to rotate, and thereby steer, the guidewire while it is being advanced through a patient's vascular system.

A major requirement for guidewires and other guiding members is that they be flexible enough to avoid damaging the blood vessel or other body lumen through which they are advanced. However, they also must have sufficient column strength to be pushed through a patient's vascular system or other body lumen without kinking. These characteristics are especially difficult to achieve when designing guidewires capable of crossing relatively tight lesions, particularly with chronic total occlusions (CTO's). Conventional guidewires typically do not have distal tips capable of crossing such lesions.

Accordingly, there is a need for guidewire designs that facilitate the crossing of relatively tight lesions without sacrificing handling characteristics. The present invention satisfies these and other needs.

SUMMARY OF THE INVENTION

The present invention is directed to a guidewire or other guiding member having a tapered distal coil. Generally, the guidewire comprises an elongated core member having a proximal section and a distal section and a coil disposed about and secured to the distal core section. The coil has a distal portion which tapers distally to the distal end thereof. At least part of the tapered distal portion of the coil is provided with a polymer coating which bridges or encapsulates individual turns of the coil.

The polymer coating covers the coil a distance of at least about 1.5 cm and may extend the entire length of the coil, e.g. up to a distance of about 40 cm from the distal end of the coil and preferably a distance of about 2 to about 12 cm from the distal end of the coil. The polymer coating has a thickness of about 0.0001 inch to 0.004 inch (0.0025 mm to 0.1 mm).

The outer diameter of the distal portion of the coil may taper from about 0.001 inch to 0.035 inch (0.0025 cm to 0.089 cm), to an outer diameter of about 0.006 inch to about 0.02 inch (0.15–0.51 mm), preferably about 0.008 inch to about 0.014 inch (0.2–0.36 mm). The tapered portion of the coil is about 1 cm to about 10 cm in length, preferably about 2 to about 5 cm in length. The entire coil length may range from about 3 to about 40 cm, preferably about 10 to about 30 cm.

The tapered coil, particularly with the polymer coating which bridges or encapsulates the turns of the coil, facilitates advancement through tight lesions such as CTO's. The polymer coating provides a smoother surface than the coil turns alone, and fixes the turns of the coil for a more damage tolerant distal tip.

These and other features of the invention will become more apparent from the following detailed description of the invention and the accompanying exemplary drawings.

BRIEF DESCRIPTION OF THE DRAWINGS

FIG. 1 is a schematic, elevational view of a guidewire embodying features of the invention.

FIG. 2 is a transverse cross sectional view of the guidewire shown in FIG. 1 taken along the lines 2—2.

FIG. 3 is a longitudinal cross sectional view taken through the tapered portion of the coil illustrating the polymer bridge between the turns of the coil.

FIG. 4 is a schematic, elevational view of a core member which may be suitable for the guidewire shown in FIG. 1.

DETAILED DESCRIPTION OF THE INVENTION

FIGS. 1–3 illustrate a guidewire 10 embodying features of the invention that is adapted to be inserted into a patient's body lumen, such as an artery or vein. The guidewire 10 comprises an elongated, core member 11, having a proximal core section 12 and a distal core section 13 and a helical coil 14 which is disposed about and secured to the core member 11 at its distal end by welding or soldering which forms the rounded plug 15. The coil 14 has a distal portion 16 which tapers distally to the distal end of the coil 14 secured to the rounded plug 15. The proximal end 17 of the coil 14 is secured by suitable means such as soldering to the core member 11. The coil 14 may also be secured at an intermediate location 18 at the junction between the tapered distal portion 16 and the constant diameter proximal coil portion 19 by suitable means such as soldering.

If desired, lengths of the coil can be stretched, for example from about 5 to about 50 percent, preferably about 10 to 30 percent of the length, to impart greater flexibility and also facilitate encapsulation by the polymeric layer. As known in the art, helical coil 14 can comprise a plurality separate coils, such as intermediate and tip coils, configured with screw stretches to facilitate securing them together. The ends of the coils may have the turns of the coil stacked together as desired.

At least the tapered distal portion 16 of the helical coil 14 and preferably the entire length of coil 14 has a polymer coating or layer 20, which may be applied by spray coating, dip coating or other suitable means, to either encapsulate the tapered distal coil portion 16 or to at least bridge the turns of the tapered portion of the coils. The coating is preferably a urethane, but other polymers may be used. Presently preferred polymers include black and clear thermoset aliphatic polyurethanes. The polymer coating reduces the friction of the coil, imparting a more lubricious and effortless feel to the guidewire, improving its handling. The polymer coating also locks the intermediate and tip coils in place, creating a more damage tolerant coil.

The polymer layer 20 bridging the space between turns of the tapered portion 16 of coil 14 is best shown in FIG. 3. The inner space defined by the interior of the tapered portion 16 of the coil 14 should not be filled with polymeric materials because the mass of polymer would prevent the necessary movement of the tapered coil portion 16 which is required to guide the tip through tight lesions.

FIG. 3 illustrates the bridging of the polymer between the turn of the tapered portion 16 of coil 14.

FIG. 4 depicts the elongated core member 11 of the guidewire 10 shown in FIG. 1. The distal section 13 of the elongated core member 11, has distally tapered portions 21 and 22 that become smaller in the distal direction followed by cylindrical sections 23 and 24 of constant diameters. Preferably, there is a final manually shapeable flat section 25 at the distal end of core member 11.

The core member can be formed from high strength materials such as stainless steel, or other high modulus materials, or can be formed from superelastic or shape memory materials, such as nickel titanium alloys. The core member 11 may have a coating (not shown) of lubricous material such as a fluoropolymer (sold under the trademark Teflon(r) by DuPont, de Nemours & Co.) or other suitable lubricous coatings such as other fluoropolymers, hydrophilic coatings and polysiloxane coatings. The coil 14 may be formed of suitable materials such as those from which the core is made or radiopaque materials such as platinum, palladium, tungsten and alloys thereof.

Various dimensions are suitable for the practice of this invention and may be adapted as desired for particular applications. In one embodiment designed for coronary artery uses, the overall length of guidewire 10 may be about 150 cm to 300 cm, but typically is 190 cm. The proximal portion 12 of the core member has an outer diameter of about 0.008 inch to 0.035 inch (0.2–0.9 mm), preferably about 0.01 to about 0.014 inch (0.25–0.36 mm). The tapered sections 21 and 22 may have lengths of about 3.0 cm to 6.0 cm and cylindrical sections 23 and 24 may have lengths of about 3.0 cm to 20.0 cm. The distal cylindrical portion 24 has a diameter of about 0.0028 inch to 0.0037 inch (0.071 cm to 0.094 cm). The flattened portion 25 preferably has a thickness of about 0.0015 inch to about 0.0031 inch (0.038–0.079 mm) and a length of about 0.5 to about 1 cm. Helical coil 14 may generally be formed from round wire having a diameter of about 0.0015 inch to 0.006 inch (0.038–0.15 cm) or from ribbon wire having a rectangular cross section with dimensions of about 0.0005 inch by 0.0015 inch (0.013–0.038 cm) to 0.002 inch by 0.006 inch (0.051–0.15 mm). The length of the coil can range from about 0.5 cm to the entire length of the device, with a preferred range of 1.0 cm to about 30.0 cm. The distal tapered coil section may have a length of about 1 to about 40, preferably 5 about 2 to about 12, with 3 cm being one present embodiment. At the proximal end of the coil 14, the outer diameter can range from about 0.01 inch to 0.30 inch (0.25–7.62 mm), preferably from about 0.010 inch to 0.018 inch (0.025 cm to 0.046 cm). At the distal end, the coil 14 can have a diameter ranging from about 0.006 to about 0.014 inch (0.15–0.35 mm), preferably about 0.008 inch to about 0.012 inch (0.20–0.3 mm), typically about 0.010 inch (0.025 cm). In particular, the use of ribbon wire, having a rectangular cross section, allows a reduced tip diameter such as about 0.008 inch (0.020 cm) when using wire with dimensions of 0.001 inch by 0.003 inch (0.025–0.076 mm). The polymer coating 20 may have a thickness from about 0.0001 inch to 0.004 inch (0.0025–0.10 mm). The polymer coating may cover just the tapered distal tip coils, or the tapered distal tip and the intermediate coils or the full length of the guidewire. The coating covers the coil a distance of about 1.5 cm to 40 cm from the distal end of the coil, preferably about 2 to about 12 cm, from the distal end of the coil. The coating 20 may be one or multiple polymer layers of the same or different polymeric materials.

It will be apparent from the foregoing that, while particular forms of the invention have been illustrated and described, various modifications can be made without departing from the spirit and scope of the invention. Moreover, those skilled in the art will recognize that features shown in one embodiment may be utilized in other embodiments.

What is claimed is:

1. An intravascular guidewire comprising:
an elongated core member having a proximal core section, a distal core section and a coil, the coil having a tapered distal portion with a tapered distal end, the coil disposed about the distal core section of the core member and secured at the distal end to the distal core section and having a polymer coating covering only the tapered distal portion so as to bridge individual turns of the coil.

2. An intravascular guidewire comprising:
an elongated core member having a proximal core section, a distal core section and a coil, the coil having a distal end and a distally tapered distal portion leading to the distal end, the coil disposed about the distal core section of the core member and secured by at least the distal end to the distal core section and having a polymer coating covering the tapered distal portion so as to encapsulate individual turns of the coil a distance of not more than about 40 cm from the distal end of the coil.

3. The guidewire of claim 2, wherein the polymer coating is a polyurethane.

4. The guidewire of claim 2, wherein the polymer coating includes multiple layers of polymeric coatings.

5. The guidewire of claim 4, wherein the multiple layers of polymeric coatings are the same polymeric material.

6. The guidewire of claim 4, wherein the multiple layers of polymeric coatings are different polymeric materials.

7. The guidewire of claim 4, wherein the polymeric coating that contacts the coil is a polyurethane.

8. An intravascular guidewire comprising:
an elongated core member having a proximal core section, a distal core section and a coil, the coil having a distal end and a distally tapered distal portion leading to the distal end, the coil disposed about the distal core section of the core member and secured by at least the distal end to the distal core section and having a polymer coating covering the tapered distal portion so as to encapsulate individual turns of the coil a distance of about 2 to about 12 cm from the distal end of the coil.

* * * * *